(12) United States Patent
Bochenek

(10) Patent No.: US 11,759,408 B2
(45) Date of Patent: Sep. 19, 2023

(54) DENTAL HYGIENE WIPES COMPRISING MICROCAPSULES

(71) Applicant: Stephane Bochenek, Yerres (FR)

(72) Inventor: Stephane Bochenek, Yerres (FR)

( * ) Notice: Subject to any disclaimer, the term of this patent is extended or adjusted under 35 U.S.C. 154(b) by 0 days.

(21) Appl. No.: 16/634,101

(22) PCT Filed: Jul. 20, 2018

(86) PCT No.: PCT/EP2018/069844
§ 371 (c)(1),
(2) Date: Jan. 24, 2020

(87) PCT Pub. No.: WO2019/020535
PCT Pub. Date: Jan. 31, 2019

(65) Prior Publication Data
US 2020/0206093 A1   Jul. 2, 2020

(30) Foreign Application Priority Data
Jul. 24, 2017  (EP) ..................... 17182835

(51) Int. Cl.
*A61K 8/02*  (2006.01)
*A61K 8/11*  (2006.01)
*A61Q 11/00*  (2006.01)

(52) U.S. Cl.
CPC .............. *A61K 8/0208* (2013.01); *A61K 8/11* (2013.01); *A61Q 11/00* (2013.01)

(58) Field of Classification Search
CPC .......... A61Q 11/00; A45D 44/18; A61K 7/16
USPC ..................................... 424/10, 49
See application file for complete search history.

(56) References Cited

U.S. PATENT DOCUMENTS

| | | | | |
|---|---|---|---|---|
| 3,957,964 A | * | 5/1976 | Grimm, III | A61K 8/11 424/10.4 |
| 5,064,650 A | * | 11/1991 | Lew | A61Q 11/00 424/435 |
| 2003/0120180 A1 | * | 6/2003 | Kaylor | A61B 42/20 600/584 |

* cited by examiner

*Primary Examiner* — Walter E Webb

(57) ABSTRACT

The invention relates to a dental cleaning wipe comprising a non-woven textile support impregnated with a dental hygiene composition containing mechanically-broken microcapsules, the content of which is released by breaking the wall, as well as controlled-release microcapsules, the content of which is released by permeation through the wall, the walls of said microcapsules being water-insoluble.

6 Claims, No Drawings

DENTAL HYGIENE WIPES COMPRISING MICROCAPSULES

This invention relates to single-use, wipe-type dental hygiene products. It is generally accepted that cleaning teeth after each meal is not only desirable for good oral hygiene, but also provides a feeling of cleanliness, freshness, and oral well-being appreciated by most people.

The usual means of cleaning teeth, such as toothbrush and toothpaste, mouthwash, dental jets, etc. are not suitable for use during the day outside the home, because in addition to their bulky nature, they require access to a water point, which is not always the case.

Many dental hygiene items for people who want to clean their teeth anywhere and at any time of the day have been described in previous art. These include disposable wipe-like devices, with a textile support impregnated with a cleansing composition. Such devices can come in a variety of forms. Frequently, they are shaped like a glove finger, or folding sheet to fit the user's finger. Such devices are for example described in the U.S. Pat. Nos. 3,902,509, 4,335, 731, EP 1,267,663, or FR 3,022,134.

It has been proposed (U.S. Pat. Nos. 6,898,819; 6,721, 987; 3,902,509) to encapsulate some of the components of the cleaning composition, including aromas, to protect them from alterations in their chemical and physical properties. The encapsulation material used is water soluble and releases the contents of the capsules when in contact with moisture from the oral cavity. Because these capsules are of one type, their contents are released simultaneously.

The purpose of this invention is to provide dental wipes that provide both an immediate effect of cleanliness and freshness, and a persistent deferred effect longer after application than that of dental wipes of earlier art.

The purpose of this invention is a dental cleaning wipe consisting of a non-woven textile support impregnated with an appropriate dental hygiene composition in which at least some of the constituents are encapsulated in microcapsules deposited on the surface of the said wipe being characterized in that two different types of microcapsules are associated: immediate-release microcapsules, and deferred-release microcapsules.

The first type of microcapsules (also referred to as "mechanical breakage") can release its contents by breaking the microcapsule wall due to pressure on the teeth by the user when applying the wipe. The second type of microcapsules (also referred to as "controlled diffusion") can release its contents by controlled permeation of it through the microcapsule wall.

The main advantage of combining these two types of microcapsules is both to provide immediate efficacy for the instantaneous release of the assets contained in mechanically broken microcapsules and to extend this efficiency in the time by permeation of the active ingredients through the walls of the Diffusion-Controlled microcapsules deposited on the teeth and gums by the friction of the wipe.

The wall of microcapsules, whether mechanically broken or diffusion-controlled, must be substantially insoluble in water in order to avoid solubilization during the preservation of the wipe by dental hygiene compositions microcapsules, these compositions generally contain a significant proportion of water. In addition, in the case of diffusion-controlled microcapsules, rapid hydro solubilization of the encapsulation membrane on contact with saliva would necessarily lead to an instantaneous release of its contents, going against the effect of deferred release wanted.

Mechanical broken microcapsules have a wall that must be strong enough not to give in to the mechanical stresses involved in the manufacture, transport and storage of the product. On the other hand, they must be able to break and release their content under pressure from the end user when applying the wipe. Thus, at least 80% of these microcapsules must be able to withstand a pressure equal to 20 g/cm2, and about 90% of these microcapsules must rupture at a pressure equal to 500 g/cm2.

Controlled-diffusion microcapsules should not break under pressure when the wipe is applied. They must therefore be able to withstand pressures in the order of 2,000 g/cm2.

The proportion of mechanically broken microcapsules and controlled-diffusion microcapsules can vary as a relative percentage in a ratio of 95/5 to 5/95.

The wall of the microcapsules is made from a material that is substantially insoluble in water or rendered non-water-soluble by a precipitating or reticulating agent. It is preferably composed of melamine resin with low levels of residual formaldehyde, reticulated carboxymethylcellulose (CMC), reticulated gelatin of pig skin, beef or marine collagen, polyurethane, polyamide, polyacrylate, silicone (dimethicone) or modified silicone. It may also consist of cellulose, polysaccharides, chitosane, polyols, polyvinyl alcohol, polyvinylpyrrolidone, PLGA-PLA (Poly (D, L actic-co-glycolic acid)-Poly (D, L actic Acid)) or polycaprolactone, rendered insoluble in water by crosslinking or precipitation.

Reticulant agents for insolubilizing polymers that are usually water-soluble are, for example, acid dichloride or terephthaloyl chloride (in the case of gelatin) or borax (in the case of polyvinyl alcohol), which will be used to bypass the polymer at the interface and thus form an insoluble membrane on the periphery of water droplets. Insolubilisants precipitating agents may be for example calcium or magnesium salts (cases of cellulose carboxymethyl).

Diffusion-controlled microcapsules are preferably obtained from reticulated gelatin, polyamide, or silicones. Their walls should allow their contents to be disseminated over a controllable duration depending on the average diameter and the number of micropores in their structure; this duration can vary from a few minutes to several days. The broadcast can also be controlled by the thickness of the wall and porosity of the microcapsule wall are determined to allow sufficient sealing under normal storage conditions, but a gradual release of their contents for a period of several minutes to a few hours, due to oral temperature and/or saliva.

Microcapsules can be prepared by processes known in themselves to the tradesman. In most cases, depending on the conditions chosen for the implementation of the process, mechanically broken microcapsules or diffusion-controlled microcapsules can be obtained. Non-limiting examples include complex coacervation encapsulation, in situ polymerization encapsulation and interfacial polymerization encapsulation.

a) Encapsulation by Complex Coacervation

Microcapsules are obtained by formation of a gelatin complex and anionic polymer (CMC, polyphosphate, alginate, gum arabic, etc. . . . ) under the influence of pH.

The presence of an anionic polymer called protective colloid is mandatory to obtain isolated capsules or clusters.

The process consists of 5 steps

Emulsion
Coacervation
Compaction
Cross linking
Rise in temperature and adjustment of the pH This results in flexible and transparent capsules, with a diameter ranging from 1 µm to 500 µm.

Depending on their degree of reticulation and size, these capsules can be waterproof and break by applying a specific pressure (mechanical break capsules) or permeable, allowing a controlled release with a release speed that can be adjusted as needed.

Larger capsules tend to generate greater porosity of the walls, creating more favorable conditions for controlled permeation of the assets.

b) In Situ Resin Polymerization Encapsulation

This process allows the release of the asset by the breakage of the envelope with an adjustable fragility of that envelope (mechanically broken microcapsules).

The production of microcapsules by polymerizing the envelope is obtained in the watery phase from a polymer solution that becomes insoluble and precipitates around the drops of an oily or low-water-soluble compound under the effect of a change in pH, temperature or by adding a reticulating agent.

The operation is done in 2 steps modulated by pH and temperature:
  Emulsion and polymerization: it is the polymer in formation that stabilizes the emulsion
  Cross linking It also requires the presence of an anionic polymer called colloid Protector.

Melamine and urea formol resins are the main ones used.

The release of the active ingredients is obtained by mechanical breakage of the envelope; the fragility of the microcapsule wall is adjustable according to the crosslinking time.

These hard and opaque microcapsules have a very good sealing and a very good chemical resistance, with an average diameter between 1 µm and 200 µm.

c) Encapsulation by In Situ Polymerization of Silicone Resin

The principle is close to the previous one, using silicone or functionalized silicone monomers.

Flexible and transparent capsules are obtained, with a diameter of between 1 µm and 500 µm.

Depending on the degree of reticulation and their size, these capsules can release their contents by breaking the envelope, or by allowing a controlled release.

d) Interfacial Polymerization Encapsulation

The principle is the formation of a polymer by reaction between two monomers or prepolymers, one of the two products being in the water phase and the other in the oily phase.

The process takes place in two steps modulated by pH and temperature:
  Emulsion and polymerization: it is the polymer in formation that stabilizes the emulsion;
  Crosslinking.

The main polymers used are polyurethanes (diisocyanate+diamine) and polyamides (diacid chloride+diamine).

This process allows for mechanically broken microcapsules, but also, if desired, Diffusion-controlled microcapsules if the wall thickness is made thinner, notably by reducing the reticulation time.

The dental wipes compliant with the invention can come in different forms, for example in the form of flat sheets. However, they preferably come in the form of a glove finger.

The non-woven medium used in these dental wipes is preferably made of cellulose, chemically modified cellulose or an absorbent material derived from cellulose.

Especially when the wipes are in the form of a glove finger, the unwoven holder is welded or glued to a layer of waterproof film, positioned on the inside side of the glove finger. This waterproof film forms a barrier to protect the user's finger from saliva, as well as to prevent the spread inside the glove finger of the composition impregnating the unwoven medium. This barrier film can be made up, as non-limiting examples, of PVC, polyethylene, polypropylene, polyamide, complex films co-extruded, etc. . . .

The non-woven medium has a thickness of between 20 and 1500 µm, preferably at least twice the average diameter of the microcapsules deposited on its surface. When the process of manufacturing and storing of the non-woven medium involves coiling, the resistance of the microcapsule associated with the elasticity of the non-woven medium must allow to absorb coil pressure up to 20 g/cm2 without premature failure of the microcapsules.

The average diameter of microcapsules containing the active ingredients useful for invention is between 1 and 500 µm, preferably between 1 and 50 µm, preferably still between 2 and 20 µm.

The amount of microcapsules deposited on the unwoven medium is in the order of 5 to 50 g/m2 of surface area of the unwoven medium.

The dental hygiene composition impregnating the non-woven material may contain various constituents chosen from those usually used in oral hygiene compositions; non-limiting examples include, for example, tensioactive agents, polishing agents, whitening agents, anti-plate agents, anti-caries, antiseptic agents, flavouring agents, etc. . . . . . Generally, some of the components are included in the microcapsules, and the other part directly permeates the unwoven medium. The components included in the microcapsules will generally be flavoring and/or antiseptic agents, such as plant species, and, if necessary, anti-plate agents, and/or anti-cavities agents.

These microcapsules are attached to the surface of the non woven material by spraying, soaking, bedding or coating.

In order to improve their stability and non-woven adhesion properties, these microcapsules can be associated with adjuvants such as: binders, emulsifiers, preservatives up to 30% in mass compared to that of microcapsules.
  Emulsients: e.g. polysorbate 80 (ethoxylated sorbitan ester), hydrogenated lecithin, glycerol monostearate, etc. . . .
  Binders (0.5 to 1.5% mass): all agents whose thickening and stabilizing properties increase the adhesive power of microcapsules on the unwoven material, such as: carboxymethylcellulose, cellulose gum, xanthan gum, etc. . . .
  Preservatives: e.g. isothiazolinone derivatives, sodium benzoate, potassium sorbate, EDTA, dehydroacetic acid, etc. . . .

This invention will be better understood using the following description supplement, which refers to non-limiting examples illustrating the preparation of dental wipes in accordance with the invention.

EXAMPLE 1: DISINFECTANT DENTAL CLEANER 1

| Component | % in microcapsule | % in formula |
|---|---|---|
| Purified Water | | 71.20 |
| Glycerin | | 5.00 |
| Xylitol | | 0.50 |
| Sorbitol | | 2.00 |

-continued

| Component | % in microcapsule | % in formula |
|---|---|---|
| Cocoyl glucoside | | 0.20 |
| Sodium Benzoate | | 0.30 |
| Sodium citrate | | 0.80 |
| Diffusion-Controlled silicone microcapsules medium diameter 5 μm containing: | | 7.00 |
| Melaleuca Alternifolia Essential Oil | 10.00 | |
| Peppermint essential oil | 30.00 | |
| Essential Oil Lemon | 60.00 | |
| Crosslinked gelatin microcapsules with an average diameter of 15 μm with mechanical rupture containing: | | 13.00 |
| Essential Oil Lemon | 70.00 | |
| Peppermint essential oil | 30.00 | |
| TOTAL | | 100.00 |

Diffusion-Controlled silicone microcapsules are prepared by in situ polymerization.

Mechanically broken gelatin microcapsules are prepared by complex coacervation in the presence of alginate.

A finger-shaped wipe, consisting of a 50 μm thick layer of cellulose, lined with a 20 μm thick waterproof film, was impregnated by scarfing with the composition shown in the table above, this composition being prepared by a simple cold mixture; both types of microcapsules, both in the form of a thick water yawn suspension at a concentration of about 35% of dry capsules, are added at the end of mixing under low agitation.

EXAMPLE 2: DENTAL CLEANSER 2

| Component | % in microcapsule | % in formula |
|---|---|---|
| Purified Water | | 81.90 |
| Glycerin | | 3.00 |
| Xylitol | | 0.80 |
| Sodium bicarbonate | | 2.00 |
| Sodium Benzoate | | 0.30 |
| Potassium Sorbate | | 0.20 |
| Carboxymethyl cellulose | | 1.20 |
| Polysorbate 80 | | 0.60 |
| Diffusion-controlled silicone microcapsules medium diameter 5 μ containing: | | 7.00 |
| Essential Oil Eucalyptus Globulus | 30.00 | |
| Essential Oil Lemon | 70.00 | |
| Reticulated fish gelatin microcapsules average diameter 15 μ mechanical rupture containing: | | 3.00 |
| Essential Oil Eucalyptus Globulus | 30.00 | |
| Essential Oil Lemon | 70.00 | |
| TOTAL | | 100.00 |

Silicone microcapsules with controlled diffusion are prepared by polymerization in situ.

Mechanically broken gelatin microcapsules are prepared by complex coacervation in the presence of cellulose carboxymethyl.

A finger-shaped wipe, consisting of a 50 μm thick cellulose layer, lined with a 20 μm thick waterproof film, was impregnated by spraying the cellulosic part with the composition shown in the table above, the non-microcapsule composition prepared by a simple mixture at a temperature of 45° C.; after cooling to a maximum of 30° C., the microcapsules are added under low agitation. Diffusion-controlled silicone microcapsules are integrated into a thick water suspension at the 35% concentration of dry capsules and mechanically broken fish gelatin microcapsules are found under form of dry capsules and are introduced at the end of the mixing process.

EXAMPLE 3: DISINFECTANT DENTAL CLEANSER 3

| Component | % in microcapsule | % in formula |
|---|---|---|
| Purified Water | | 82.92 |
| Glycerine | | 5.00 |
| Acesulfame potassium | | 0.05 |
| Fluoride sodium | | 0.03 |
| Benzoate sodium | | 0.20 |
| Carboxymethyl cellulose | | 1.20 |
| Polysorbate 80 | | 0.60 |
| Microcapsules silicones with diffusion - controlled medium diameter 5 μ containing: | | 7.00 |
| Peppermint essential oil | 100.00 | |
| Reticulated fish gelatin microcapsules average diameter 40 μ low thickness mechanical rupture containing: | | 3.00 |
| Chlorhexidine digluconate | 2.00 | |
| Lemon Essential Oil | 98.00 | |
| TOTAL | | 100.00 |

Diffusion-controlled silicone microcapsules are prepared by in situ polymerization.

Mechanically-broken microcapsules in low-thickness gelatin are prepared by complex coacervation in the presence of alginate.

A finger-shaped wipe, consisting of a 50 μm thick cellulose layer, lined with a 20 μm thick waterproof film, was impregnated by spraying the cellulosic part with the composition shown in the table above, the non-microcapsule composition being prepared by a simple mixture at a temperature of 45° C.; after cooling to a maximum of 30° C., the microcapsules are added under low agitation. Diffusion-controlled silicone microcapsules are integrated into a thick water suspension at the 35% concentration of dry capsules and mechanically broken fish gelatin microcapsules come in the form of dry capsules and are introduced at the end of the mixing process.

EXAMPLE 4: DENTAL CLEANSER 4

| Component | % in microcapsule | % in formula |
|---|---|---|
| Purified water | | 83.70 |
| Carbomer 940 | | 1.80 |
| Xylitol | | 0.80 |
| Sodium bicarbonate | | 2.00 |
| Sodium Benzoate | | 0.30 |
| Triethanolamine | | 0.30 |
| Camomile extract | | 0.50 |
| Carraghenane | | 0.60 |
| Microcapsules reticulated gelatin with diffusion-controlled medium diameter 2 μ containing: | | 7.00 |
| Peppermint essential oil | 80.00 | |
| Sweet Orange Essential Oil | 20.00 | |

-continued

| Component | % in microcapsule | % in formula |
|---|---|---|
| Medium Diameter Polyamide Microcapsules 18 u mechanically broken containing: | | 3.00 |
| Sweet Orange Essential Oil | 30.00 | |
| Lemon Essential Oil | 70.00 | |
| TOTAL | 100.00 | |

Diffusion-controlled reticulate microcapsules are prepared by complex coacervation.

Polyamide mechanically laid microcapsules are prepared by polymerization in situ.

A finger-shaped wipe, consisting of a 40 μm thick layer of cellulose, was sprayed with the composition shown in the table above, the non-microcapsule composition being prepared by simple mixture at a temperature of 45° C.; after cooling to a maximum of 30° C., the microcapsules are added under low agitation. Both types of microcapsules are integrated in the form of a thick slimy suspension water yawn suspension (slurry) at a concentration of 40% of dry capsules.

The invention claimed is:

1. Dental cleaning wipe consisting of a non-woven textile support impregnated with a dental hygiene composition in which at least some of the constituents are encapsulated in microcapsules deposited on the surface of the said non-woven textile support being characterized in that it includes two different types of microcapsules:

mechanically broken microcapsules, the contents of which are released by breaking of the wall; and Diffusion-controlled microcapsules whose contents are released by permeation through the wall, and in that the wall of these microcapsules is insoluble in water.

2. Dental cleaning wipe according to claim 1, characterized in that said wipe comes in the form of a glove finger.

3. Dental cleaning wipe according to one of the claim 1 or 2, characterized in that the non-woven textile support is chosen from cellulose, chemically modified cellulose and cellulose-derived absorbent materials.

4. Dental cleaning wipe according to claim 1, characterized in that the thickness of the non-woven textile support is between 20 and 1500 μm, and is at least 2 times the average diameter of the microcapsules deposited on its surface.

5. Dental cleaning wipe according to claim 1, characterized in that the average diameter of the microcapsules deposited on its surface is between 1 and 50 μm.

6. Dental cleaning wipe according to claim 1, characterized in that the amount of microcapsules deposited on the non-woven textile support is 5 to 50 g/m2 of surface of the non-woven textile support.

* * * * *